United States Patent
Brod

(10) Patent No.: US 11,643,460 B2
(45) Date of Patent: May 9, 2023

(54) ADMINISTRATION OF AN ANTI-INTERLEUKIN 12/23 ANTIBODY FOR TREATMENT OF AUTOIMMUNE DISEASE

(71) Applicant: Staley Brod, Bellaire, TX (US)

(72) Inventor: Staley Brod, Bellaire, TX (US)

( * ) Notice: Subject to any disclaimer, the term of this patent is extended or adjusted under 35 U.S.C. 154(b) by 823 days.

(21) Appl. No.: 14/525,951

(22) Filed: Oct. 28, 2014

(65) Prior Publication Data
US 2016/0115227 A1     Apr. 28, 2016

(51) Int. Cl.
*C07K 16/24*     (2006.01)
*A61K 45/06*     (2006.01)
*A61K 39/00*     (2006.01)

(52) U.S. Cl.
CPC ............ *C07K 16/244* (2013.01); *A61K 45/06* (2013.01); *A61K 2039/505* (2013.01); *C07K 2317/21* (2013.01); *C07K 2317/76* (2013.01)

(58) Field of Classification Search
None
See application file for complete search history.

(56) References Cited

U.S. PATENT DOCUMENTS 7,776,331 B1 *   8/2010   Chartash .............. C07K 16/244
                                                   424/130.1

OTHER PUBLICATIONS

The FDA Guideline for Industry Dose-response Information to Support Drug Registration (ICH-E4, Nov. 1994).*
Reilly et al. (Clin. Pharmacokinet. Apr. 1997; 32 (4): 313-323).*
ClinicalTrials.gov study NCT01645280 (downloaded from https://clinicaltrials.gov/archive/NCT01645280/2012_08_08; updated Aug. 8, 2012).*
Vajdos et al. (J Mol Biol. Jul. 5, 2002;320(2):415-28 at 416).*
Brown et al. (J Immunol. May 1996;156(9):3285-91).*
Ma (Modern Drug Discovery 2004, 7(6)).*
Blumberg et al. (Nat Med.; 18(1): 35-41).*
Steinman et al. (Nat Med. Jan. 6, 2012;18(1):59-65).*
Koutruba et al (Ther Clin Risk Manag. Apr. 15, 2010;6:123-41) (Year: 2010).*
Blumberg et al. (Nat Med.;18(1):35-41) (Year: 2015).*

* cited by examiner

*Primary Examiner* — Brian Gangle
*Assistant Examiner* — Andrea K McCollum
(74) *Attorney, Agent, or Firm* — Benjamin Aaron Adler

(57) ABSTRACT

The present invention provides a method for treating or delaying the onset of an autoimmune condition in a human subject. An effective oral dose of ustekinumab is administered to the subject. Oral administration of ustekinumab also is useful in a method of decreasing innate inflammatory cytokines, such as Interleukin-1β and Tumor Necrosis Factor-α, Th1-like cytokines Interleukin-2 and Interferon-γ, Interleukin-17 ($T_{eff}$), Interleukin-12p70, and increasing Th2-like counter-regulatory cytokine Interleukin-13 in a subject.

9 Claims, 6 Drawing Sheets

Specification includes a Sequence Listing.

SEQUENCE LISTING

```
<160> NUMBER OF SEQ ID NOS: 1

<210> SEQ ID NO 1
<211> LENGTH: 21
<212> TYPE: PRT
<213> ORGANISM: Artificial sequence
<220> FEATURE:
```

```
<222> LOCATION: 35..55
<223> OTHER INFORMATION: Sequence of myelin oligodendrocyte glycoprotein
      peptide

<400> SEQUENCE: 1

Met Glu Val Gly Trp Tyr Arg Ser Pro Phe Ser Arg Val Val His Leu
1               5                   10                  15

Tyr Arg Asn Gly Lys
            20
```

ADMINISTRATION OF AN ANTI-INTERLEUKIN 12/23 ANTIBODY FOR TREATMENT OF AUTOIMMUNE DISEASE

BACKGROUND OF THE INVENTION

Field of the Invention

The present invention relates generally to the fields of autoimmune diseases. More specifically, the present invention relates to uses of ingested (orally administered) anti-interleukin 12/23 antibody in the treatment of autoimmune diseases.

Description of the Related Art

The following abbreviations may be used herein: ACTH—adrenocorticotropin hormone, a-MSH—alpha-melanocyte stimulating hormone. EAE—experimental autoimmune encephalomyelitis, DTH—delayed type hypersensitivity, DPBS—Dulbecco's phosphate buffered saline, GALT—gut associated lymphoid tissue, QoL—quality of life, PP—Peyer's Patch, SIRS—soluble immune response suppressor, SPF—specific pathogen free, SST—somatostatin, TCZ—tocilizumab, $T_{reg}$—T regulatory cell, UTZ—ustekinumab.

Experimental autoimmune encephalomyelitis is a T cell mediated inflammatory autoimmune process of the CNS that resembles in some aspects the human demyelinating disease multiple sclerosis (MS) (1) and provides a useful animal model for the evaluation of potential therapies for cell mediated autoimmune diseases (2-4). Ingested proteins such as type I IFN (5), SIRS peptide 1-21 (6), a-MSH (7), ACTH (8) and SST (9) inhibit attacks and inflammation in acute experimental autoimmune encephalomyelitis (5, 10). Oral antibodies against cytokines such as IL-6 also have similar effect in experimental autoimmune encephalomyelitis (11).

Psoriasis is a chronic inflammatory disorder characterized by T cell dysregulation and a chronic inflammatory infiltrate within the epidermis that variably affects the skin, nails, and joints (12). Investigators have identified IL-12 and IL-23 of the Th1 and Th17 inflammatory pathways as key mediators of psoriasis (13).

Interleukins 12 and 23 have important roles in the pathophysiology of psoriasis (12). A new class of biological drug shows promise in long-term disease control for psoriasis patients, a fully human monoclonal antibody (UTZ) that binds with high affinity to the shared p40 subunit of IL-12 and IL-23 (14). Ustekinumab has been studied in psoriasis, psoriatic arthritis, Crohn's disease and multiple sclerosis (15-17). Ustekinumab seems to be efficacious for the treatment of moderate-to-severe psoriasis for at least a year in most patients (18), significantly improving physical function and QoL in patients with psoriatic arthritis (19) with similar efficacy to etanercept (20, 21) and a favorable safety profile (22-25) Ustekinumab also works in anti-TNF-experienced PsA patients (26).

Therefore, the prior art is deficient in the use of oral, ingested anti-interleukin 12/23 antibody in the treatment of autoimmune diseases such as multiple sclerosis. The present invention fulfills this long-standing need and desire in the art.

SUMMARY OF THE INVENTION

The present invention is directed to a method for treating or delaying the onset of an autoimmune condition in a human subject comprising orally administering to the subject an effective dose of an anti-interleukin 12/23 antibody.

The present invention is further directed to a method of decreasing innate inflammatory cytokines IL-1β and TNF-α, Th1-like cytokines IL-2 and IFN-γ, IL-17 ($T_{eff}$), IL-12p70 and increasing the Th2-like counter-regulatory cytokine IL-13 in a human subject comprising orally administering to the subject an effective dose of an anti-interleukin 12/23 antibody.

BRIEF DESCRIPTION OF DRAWINGS

The following drawings are part of the present specification and are included to further demonstrate certain aspects of the present invention. The invention may be better understood by reference to the drawings in combination with the detailed description of specific embodiments presented herein.

DETAILED DESCRIPTION OF THE INVENTION

Figure 1:
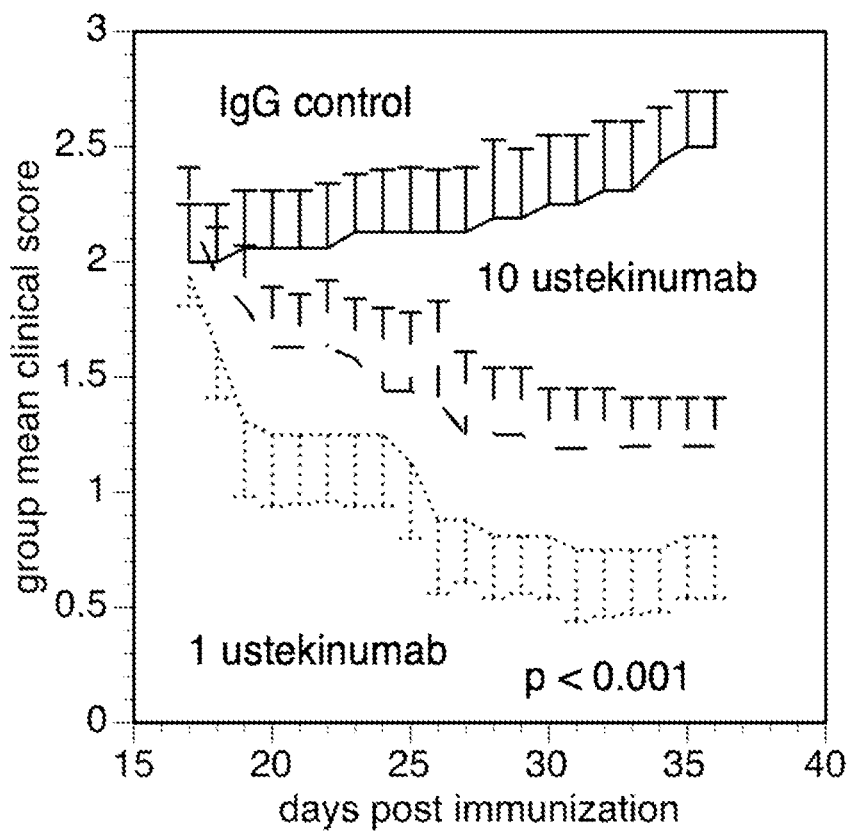
FIG. 1 shows that ingested ustekinumab inhibits EAE attacks. B6 mice (n=8/group) were immunized with MOG peptide 35-55 and were gavaged with 0.1 ml of 1 μg or 10 μg IgG isotype control or 1 mg or 10 mg ustekinumab as described below. Both 1 and 10 mg ingested ustekinumab significantly inhibits EAE progression compared to control ($p<0.001$, ANOVA, day 17-36, group score±SEM) (1 mg IgG isotype control shown; 10 mg not significantly different and not shown). The figure shows combined results from 3 separate experiments (total n=24/group).

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

Treatment of chronic autoimmune disease is challenging even with the advent of new therapeutic techniques. Typical therapies involve the administration of immunosuppressive agents such as steroids. Though steroids are typically not highly effective, they are well tolerated for long term use and many may be administered orally. A non-invasive method for administration, such as oral administration, is highly preferred in cases of chronic diseases such as multiple sclerosis.

The studies described here clearly demonstrate that orally administered and/or ingested anti-interleukin 12/23 antibody can be used as a therapeutic treatment for autoimmune disease. The EAE mouse model is a well established model system for the study of human autoimmune disease, more specifically multiple sclerosis. Studies herein show that anti-interleukin 12/23 antibody may be orally administered to mice over an extended time period with no detectable toxicity. Furthermore, the oral anti-interleukin 12/23 antibody administration significantly reduced clinical symptoms of autoimmune disease as compared to a placebo control in the murine EAE model system. Thus, these studies provide the basis for a new enteral formulations of anti-interleukin 12/23 antibody for the treatment of autoimmune disease.

Clinical severity of disease symptoms, e.g. limb weakness, ataxia, and paraplegia, may be evaluated in various ways. In one embodiment of the invention, clinical severity is graded on a numerical scale corresponding to the number or severity of symptoms observed. In a specific embodiment of the invention, clinical symptoms in a murine model are quantified as follows: 0=no disease; 1=minimal or mild hind limb weakness (associated with limp tail); 2=moderate hind limb weakness or mild ataxia (waddling gait and/or poor righting ability); 3=moderate to severe hind limb weakness; 4=severe hind limb weakness or moderate ataxia; 5=paraplegia with no more than moderate four limb weakness; 6=paraplegia with severe four limb weakness or severe ataxia. In another embodiment of the invention, disease symptoms are evaluated by number of inflammatory foci per CNS segment or area. In a very specific embodiment, these evaluations of inflammatory foci are conducted by direct visual observation of the subject CNS post-mortem.

The new methods disclosed herein address one of the greatest obstacles to treating chronic disease such autoimmune disease, that is long term tolerance of the therapeutic regimen. Such tolerance takes into account not only biological tolerance, but also tolerance in patients undergoing therapy. Injectable therapeutics are far from ideal for the treatment of chronic disease. Consent injection can result in lasting damage to the tissues around the injection site and is painful and inconvenient for patients. Additionally, injection of any substance into the body increases the risk for infection by bacteria or viruses that may be present in the therapeutic formulations or on the injection apparatus itself. The instant invention enables methods for oral administration of potent immunomodulatory polypeptides. Surprisingly, these polypeptides remain highly active in an oral formulation and are effective for treating autoimmune disease. These new oral therapeutic polypeptides are particularly well adapted for prolonged administration that is often required for the treatment of chronic disease.

Anti-interleukin 12/23 antibody compositions according to the instant invention may also be used in conjunction with other therapies that are used for the treatment of inflammation and/or autoimmune diseases. Such secondary therapies can include small molecule drugs as well as therapeutic nucleic acids or polypeptides. Anti-inflammatory agents, for example, are agents that decrease signs and symptoms of inflammation. A wide variety of anti-inflammatory agents are known to one of skill in the art. Most commonly used are the nonsteroidal anti-inflammatory agents (NSAIDs) which work by inhibiting the production of prostaglandins. Non-limiting examples include, ibuprofen, ketoprofen, piroxicam, naproxen, naproxen sodium, sulindac, aspirin, choline subsalicylate, diflunisal, oxaprozin, diclofenac sodium delayed release, diclofenac potassium immediate release, etodolac, ketorolac, fenoprofen, flurbiprofen, indomethacin, fenamates, meclofenamate, mefenamic acid, nabumetone, oxicam, piroxicam, salsalate, tolmetin, and magnesium salicylate. Another group of anti-inflammatory agents comprise steroid based potent anti-inflammatory agents, for example, the corticosteroids which are exemplified by dexamethason, hydrocortisone, methylprednisolone, prednisone, and triamcinolone as non-limiting examples. Several of these anti-inflammatory agents are available under well known brand names, for example, the nonsteroidal anti-inflammatory agents NSAIDs comprising ibuprofen include ADVIL, MOTRIN IB, NUPRIN; acetaminophens include TYLENOL; naproxen include ALEVE.

As discussed supra, certain known immunomodulatory polypeptides may also be used in accordance with the invention. Such polypeptides include, but are not limited to, SIRS, interferon-alpha and interferon-tau.

Pharmaceutical compositions of the present invention comprise an effective amount of anti-interleukin 12/23 antibody and optionally at least one additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains an anti-interleukin 12/23 antibody or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, gels (e.g., gelatin), dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

A pharmaceutical composition of the present invention comprising an anti-interleukin 12/23 antibody may also comprise different types of carriers depending on whether it is to be administered in solid, liquid or aerosol form, and whether it need to be sterile. The present invention can be administered intranasally, intravitreally, intravaginally, intrarectally, topically, mucosally, intraocularally, orally, topically, locally, via inhalation (e.g. aerosol inhalation), via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a anti-interleukin 12/23 antibody composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof. In the case of proteinacious compositions of the invention, it may also be preferable that the action of proteases be inhibited during storage of such anti-interleukin 12/23 antibody compositions. This can be accomplished by the additional of protease inhibitors and/or the storage of the compositions at low temperature prior to administration.

In embodiments where compositions according to the invention are provided in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In certain embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof an excipient, such as, for example, dicalcium phosphate, mannitol, lactose, starch, magnesium stearate, sodium saccharine, cellulose, magnesium carbonate or combinations thereof a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Methods of the invention will generally be used in an amount of an anti-interleukin 12/23 antibody effective to achieve the intended purpose. For use to treat or prevent a disease condition, ustekinumab, or pharmaceutical compositions thereof, are administered in a therapeutically effective amount. A therapeutically effective amount is an amount effective to ameliorate or prevent the symptoms, or prolong the survival of, the patient being treated. Determination of a therapeutically effective amount is well within the capabilities of those skilled in the art, especially in light of the detailed disclosure provided herein. The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs. In the case of autoimmune disorders, the drugs that may be used in combination with an anti-interleukin 12/23 antibody include, but are not limited to, steroid and non-steroid anti-inflammatory agents.

Methods for estimating dose conversions between animal models and humans have been developed. In general these algorithms have been used to extrapolate an animal dose to a dose that would be tolerated by a human. For example, method for dose conversions were disclosed by Freireich et al. (72). The conversion methods taught by Freireich calculate equivalent doses between species using surface area ($m^2$) rather than mass (kg), a method that correlates much more closely to actual data than body mass conversions. Specifically, Freireich teaches how to use an animal 10% lethal dosage ($LD_{10}$) value to estimate the maximum tolerated doses in a human. Freireich also discussed method for converting a dose in mg/kg to a dose in mg/$m^2$ by using the "km" conversion factor for the given animal.

More recent studies regarding species dose scaling have further elaborated upon the methods of Freireich. These newer studies have reduced error associated with conversion between species to determine human tolerable doses. For example, Watanabe et al. (73) describes that a conversion of doses between species using body surface area may not be the most accurate method per se for predicting a human equivalent dosage. Nonetheless, the scaling factors set forth by Watanabe yield results that are within the margin of error of the older Freireich conversions. Currently accepted methods for determining a proper starting dose in humans expand upon the methods set forth by Freireich. For example, Mahmood et al. (74) provides a discussion regarding the choice of a proper starting dose in humans given dose studies in animals.

It is an objective of the present invention to demonstrate that oral anti-interleukin 12/23 antibody has an anti-inflammatory effect in experimental autoimmune encephalomyelitis in vivo by decreasing Th17, Th1-like cytokines, increasing Th2-like cytokines without $T_{reg}$ induction in the CNS target organ in murine experimental autoimmune encephalomyelitis.

As described in detail below, the present invention is directed to a method for treating or delaying the onset of an autoimmune condition in a human subject comprising orally administering to the subject an effective dose of an anti-interleukin 12/23 antibody. In one aspect of this method, the anti-interleukin 12/23 antibody is administered in a liquid form. In one aspect of this method, the anti-interleukin 12/23 antibody is administered in a solid form. Representative examples of condition include but are not limited to rheumatoid arthritis, psoriasis, type 1 diabetes, systemic lupus erythematosus, transplant rejection, autoimmune thyroid disease (Hashimoto's disease), sarcoidosis, scleroderma, granulomatous vasculitis, Crohn's disease, ulcerative colitis, Sjogren's disease, ankylosing spondylitis, polymyositis dermatomyositis, polyarteritis nodosa, immunologically mediated blistering skin diseases, Behcet's syndrome, multiple sclerosis, systemic sclerosis, Goodpasture's disease or immune mediated glomerulonephritis. A person having ordinary skill in this are would be able to prepare satisfactory composition of an anti-interleukin 12/23 antibody and readily determine appropriate dosages for the condition to be treated. For example, an anti-interleukin 12/23 antibody may be administered in a dose from about from about 0.001 mg to about 50 mg.

In one preferred embodiment, an anti-interleukin 12/23 antibody is administered in a dose from about 3-30 mg. Generally, the anti-interleukin 12/23 antibody administration decreases levels of IL-1β, IL-2, IL-12p70, IL-13, IL-12, IL-17 ($T_{eff}$), TNF-α and IFN-γ. In a preferred embodiment, the anti-interleukin 12/23 antibody may be administered in combination with a drug such as an anti-inflammatory agent, a SIRS peptide, a-MSH, ACTH and SST. Representative examples of useful anti-interleukin 12/23 antibodies include ustekinumab and briakinumab.

In another embodiment, the present invention also provides a method of decreasing innate inflammatory cytokines IL-1β and TNF-α, Th1-like cytokines IL-2 and IFN-γ, IL-17 ($T_{eff}$), IL-12p70 and increasing the Th2-like counter-regulatory cytokine IL-13 in a human subject comprising orally administering to the subject an effective dose of an anti-interleukin 12/23 antibody. In one aspect of this method, the an anti-interleukin 12/23 antibody is administered in a liquid form. In one aspect of this method, the anti-interleukin 12/23 antibody is administered in a solid form. Representative examples of condition include but are not limited to rheumatoid arthritis, psoriasis, type 1 diabetes, systemic lupus erythematosus, transplant rejection, autoimmune thyroid disease (Hashimoto's disease), sarcoidosis, scleroderma, granulomatous vasculitis, Crohn's disease, ulcerative colitis, Sjogren's disease, ankylosing spondylitis, polymyositis dermatomyositis, polyarteritis nodosa, immunologically mediated blistering skin diseases, Behcet's syndrome, multiple sclerosis, systemic sclerosis, Goodpasture's disease or immune mediated glomerulonephritis. A person having ordinary skill in this are would be able to prepare satisfactory composition of an anti-interleukin 12/23 antibody and readily determine appropriate dosages for the condition to be treated. For example, the anti-interleukin 12/23 antibody may be administered in a dose from about from about 0.001 mg to about 50 mg. Representative examples of useful anti-interleukin 12/23 antibodies include ustekinumab and briakinumab.

Other objects, features and advantages of the present invention will become apparent from the following. It should be understood, however, that the specific examples, while indicating preferred embodiments of the invention, are given by way of illustration only, since various changes and modifications within the spirit and scope of the invention will become apparent to those skilled in the art from this detailed description.

Example 1

Materials and Methods

Induction of Active EAE

C57BL/6 6-8 week old females were actively immunized, maintained, handled and surveiled as outlined previously (6). Briefly, C57BL/6 6-8 week old females (Jackson Labs, Bar Harbor, Me.) were actively immunized by subcutaneous injection (s.c.) of 0.2 ml inoculum containing 200 μg MOG peptide 35-55 (Myelin Oligodendrocyte Glycoprotein peptide 35-55; MEVGWYRSPFSRVVHLYRNGK; SEQ ID NO: 1) in IFA (DifcoLabs, Detroit, Mich.) with 800 μg *Mycobacterium tuberculosus hominis* H37Ra (MT) on day 0 and 7 following (27), with pertussis toxin (PTx) (List Biologicals) 200 ng i.p. on day 0 and day 2 and followed for evidence of disease. Severity was graded daily as follows by a blinded observer: 0=no disease; 1=minimal or mild hind limb weakness (associated with limp tail); 2=moderate hind limb weakness or mild ataxia (waddling gait and/or poor righting ability); 3=moderate to severe hind limb weakness; 4=severe hind limb weakness or moderate ataxia; 5=paraplegia with no more than moderate four limb weakness; 6=paraplegia with severe four limb weakness or severe ataxia.

Adoptive Transfer

Thirty six days after inoculation and after peak score of attack, all spleens from each treatment group were aseptically removed, single cell suspensions prepared, and red cell lysis performed by adding 2-3 ml sterile water to single cells for 5 seconds, and once the solution became transparent, adding AIM-V media to a 50 ml tube. Splenocytes from grouped IgG isotype control fed, 1 μg or 10 μg UTZ fed mice were re-stimulated with MOG peptide 35-55 at a final concentration of 10 pg/ml for 48 hours in serum free medium (AIM-V medium, GIBCO BRL, Grand Island, N.Y.) with $2 \times 10^5$ cells/200 ml in triplicate in 96 well U-bottomed plates in a humidified 5% CO2/95% air incubator at 37° C. Splenocytes from control fed mice were also re-stimulated with MOG peptide 35-55 as described above. CD4+ T cells and monocytes/macrophage were isolated from splenocytes after MOG restimulation above using CD4 (L3T4) MicroBeads, mouse CD11b MicroBeads, human and mouse—monocyte/macrophage lineage (Miltenyi Biotec, Auburn, Calif.). Following incubation, cells were collected, washed twice in PBS, and viability determined by standard Trypan blue exclusion. Viable cells were adjusted to $10^7$ cells/0.5 ml Dulbecco's PBS immediately prior to i.p. injection into active MOG peptide 35-55 immunized recipient mice during ongoing disease (~day 17 post immunization). Following administration of ustekinumab or adoptive transfer, outcome was measured by comparing the difference between group mean active treatment and placebo group scores from day 17-31 post immunization.

Active Protein

Ustekinumab (IgG1) (UTZ) (STELERA®) was purchased from Janssen Biotech, Inc., Horsham, Pa.

Control Protein

Mouse IgG isotype control antibody (1-10 μg feeding), was purchased from Southern Biotech, Birmingham, Ala.

Dosing (Feeding) Regimen

Once non-treated inoculated mice attained a score 1.5~2.2, B6 mice were randomized to one of 3 treatment groups, and gavaged (fed) with 0.1 ml of 1 μg or 10 μg mouse IgG isotype control (mock), 1 pg, or 10 μg of ustekinumab using a 2.5 cm syringe fitted with a 22-24 gauge ball point needle (Thomas Scientific, Swedesboro, N.J.) as described [8].

Histology

Following sacrifice, cords were removed and immersion fixed in 10% neutral buffered formalin for a minimum of two weeks. After fixation, cords were sectioned in entirety in the horizontal plane at approximately 3 mm intervals and processed to paraffin. Paraffin blocks were sectioned at 6-8 microns, and step sections were stained with hematoxylin and eosin and examined by light microscopy. Cord sections were evaluated independently for foci of inflammation by an observer (SAB) (blinded) without knowledge of the treatment status of the mice prior to sacrifice. Spinal cord tissue was sampled in an identical fashion for each animal and numbers of inflammatory foci per high-powered field (HPF) (>20 perivascular lymphocytes) in the parenchyma were counted.

Measurement of Cytokine Secretion

Spleens and spinal cords (CNS) from each treatment group were aseptically removed and single cell suspensions prepared. In spinal cords, whole cords were passed through a cell strainer for CNS lymphocytes (B and D, Franklin Lakes, N.J.) and spun at 600 rpm several times to separate lymphocytes from CNS tissue. Spleen leucocytes and cord lymphocytes from grouped IgG isotype control fed or 1 mg ustekinumab fed mice were stimulated with 10 μg MOG peptide 35-55×48 hours as described (9). Murine cytokine responses were examined using a customized RAYBIO Mouse Cytokine Inflammatory Antibody Array that included innate cytokine TNF-α, IL-17 (Teff), Th1-like (IL-2, IFN-γ, IL-12p70), Th2-like cytokines (IL-4, IL-10, IL-13) and using the RayBioantibody array Analysis tool application (RayBiotech, Inc, Norcross, Ga.). Mouse TGF-b was measured using Human/Mouse TGF-b1 ELISA READY-SET-GO (eBioscience, San Diego, Calif.). Results were grouped from mice fed IgG isotype control or mice fed with ustekinumab from grouped samples of at least two separate experiments (each sample performed in duplicate) and expressed as pg/ml±SEM (student t-test).

Phenotypic Analysis

CD25 and FoxP3 expression by $CD3^+CD4^+$ lymphocytes was analyzed using the Beckman Coulter 10-Color GALLIOS Flow Cytometer and mouse regulatory T Cell Staining Kit with PE FoxP3 FJK-16s, FITC CD4, APC CD25 (eBioscience, San Diego, Calif.) following the manufacturer's instructions.

Statistics

Statistical analysis was performed using ANOVA and student t test. (Prism 4.0).

Example 2

Oral Ustekinumab Inhibits Active EAE and Donor Cells Transferred from Ustekinumab Fed Mice can Modulate Disease in Actively Immunized Recipients Preliminary experiments determined the immuno-modulatory capability of 1 and 10 mg ingested (orally administered) ustekinumab compared to IgG control in EAE. Mice were immunized and separated into 3 groups once each mouse attained a score ~2.0 (day 17 post immunization) at which time oral dosing was started. The IgG control group increased group score from day 17 and plateaued at score=2.5 36 days post immunization and 19 days after the initiation of feeding. Active treatment groups fed with 1 and 10 mg showed significant decreases in group scores after initiation of therapy (day 17) with 1 mg showing the most effect and reduction of disease severity compared to placebo (FIG. 1).

Thirty-six days following immunization, there were significantly less inflammatory foci in the 1 mg fed group compared to the IgG control fed group (Table 1, Oral).

TABLE 1

Ustekinumab fed mice and recipients of splenic, CD4+ T cell and CD11b+ cell subsets from ustekinumab fed mice have fewer inflammatory foci

|  | Control (isotype control) | Utsekinumab |
|---|---|---|
| Oral | 15.6 ± 2.0 | 8.6 ± 2.3# |
| Spleen AT | 26.5 ± 7.5 | 11.1 ± 2.6* |
| CD4+ T cell AT | 41.0 ± 5.2 | 18.8 ± 2.8# |
| CD11b+ AT | 64.1 ± 10.3 | 17.4 ± 4.7# |

Results are expressed as mean group inflammatory score ± SEM.
Control compared to active (utsekinumab 1 mg)
*p < 0.01,
p < 0.001
n = 16/group (oral, spleen).
n = 12/group (CD4+, macrophage).

Figure 2:
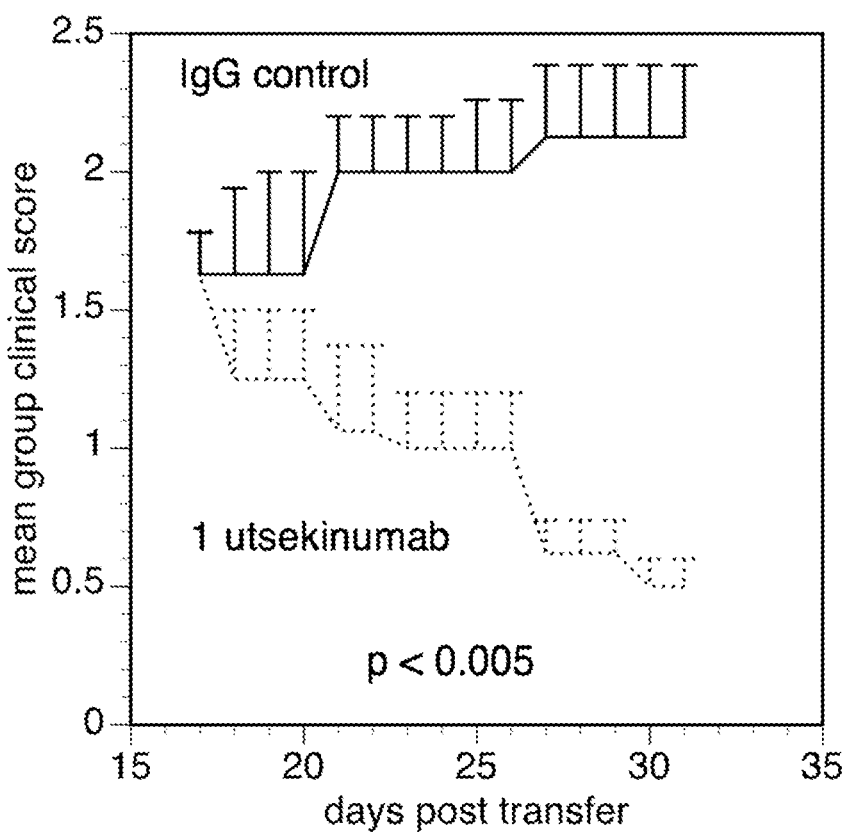
FIG. 2 shows that adoptively transferred donor cells from ustekinumab fed immunized mice protect against active EAE. Thirty six days after inoculation and after peak score of attack, spleens from IgG control and 1 mg ustekinumab fed mice were isolated and re-stimulated with MOG peptide 35-55 and adoptively transferred as described below. Recipients of IgG control fed donor cells increased their group disease severity. In contrast, recipients of ustekinumab fed donor cells decreased their group score significantly compared to recipients of IgG isotype control fed cells ($p<0.005$, day 17-31, mean group clinical group score±SEM). This experiment shows a combination of 3 separate experiments (total n=24/group).

Whether ustekinumab fed mice could passively transfer protection into actively immunized mice was examined. After adoptive transfer of MOG-restimulated splenocytes into actively immunized recipient mice with early disease on day 17 (mean group score ~1.6), recipients of donor splenocytes from IgG control fed mice increased their group disease severity over 14 days to a maximum of 2.15. In contrast, recipients of donor splenocytes from 1 mg ustekinumab fed mice decreased their group score at day 31 to a score to 0.5 (FIG. 2). Fourteen days following adoptive transfer, the number of CNS inflammatory foci in the IgG control fed group was significantly higher compared to 1 mg ustekinumab fed donors (Table 1, AT spleen control vs ustekinumab).

Figure 3:
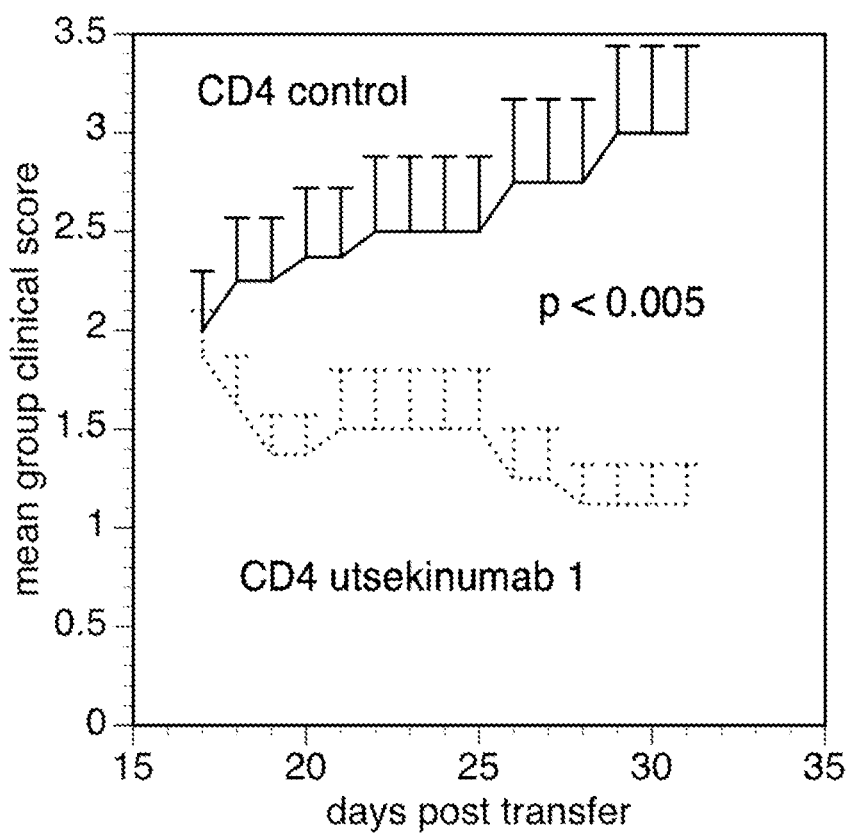
FIG. 3 shows that adoptively transferred donor CD4+ T cells from ustekinumab fed immunized mice protect against active EAE. Thirty six days after inoculation and after peak score of attack, spleens from IgG control and 1 mg ustekinumab fed mice were isolated and re-stimulated with MOG peptide 35-55, CD4+ T cells isolated and adoptively transferred as described below. Recipients of IgG control fed CD4+ T donor cells increased their group disease severity. In contrast, recipients of UTZ fed CD4+ T cells donor cells decreased their group score significantly compared to recipients of saline control cells ($p<0.005$, days 17-31, group score±SEM). This experiment shows a combination of 3 separate experiments (total n=12/group).

Adoptively Transferred CD4+ T and CD11b+ Cells from Ustekinumab Fed Donor Mice can Modulate Disease in Actively Immunized Recipients Whether a T cell subset (CD4+) from a fed donor would show immune-modulatory activity in actively immunized recipients was determined. After adoptive transfer of MOG-restimulated CD4+ T cells isolated from MOG activated splenocytes into actively immunized recipient mice with early disease on day 17 (mean group score ~2.0), recipients of donor CD4+ T cells from IgG control fed mice increased their group disease severity over 13 days to a maximum of 3.0. In contrast, recipients of donor CD4+ T cells from 1 mg ustekinumab fed mice decreased their group score at day 31 to a score=1.2 (FIG. 3).

Figure 4:
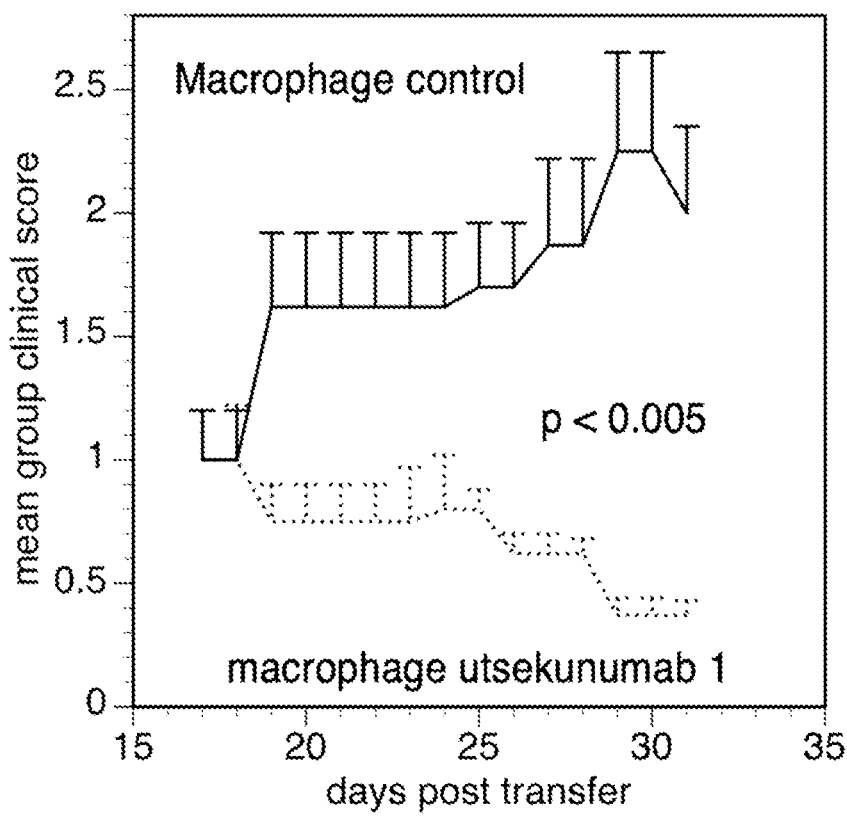
FIG. 4 shows that adoptively transferred donor CD11 b+ cells from ustekinumab fed immunized mice protect against active EAE. Thirty six days after inoculation and after peak score of attack, spleens from IgG fed control and 1 mg ustekinumab fed mice were isolated and re-stimulated with MOG peptide 35-55, CD11 b+ cells isolated and adoptively transferred as described below. Recipients of IgG control fed CD11 b+ cells increased their group disease severity. In contrast, recipients of ustekinumab fed CD11b+ donor cells decreased their group score significantly compared to recipients of saline control CD11 b+ cells ($p<0.005$, days 17-30, mean clinical group score±SEM). This experiment shows a combination of 3 separate experiments (total n=12/group).

Whether a monocyte/macrophage lineage cells (CD11b+) from a fed donor would show immune-modulatory activity in actively immunized recipients was examined. After adoptive transfer of MOG-restimulated CD11b+ cells isolated from MOG activated splenocytes into actively immunized recipient mice with early disease on day 17 (mean group score ~1.0), recipients of donor CD11b+ from IgG fed control mice increased their group disease severity over 14 days to a maximum of 2.3. In contrast, recipients of donor CD11 b+ cells from 1 mg ustekinumab fed mice decreased their group score at day 30 to a score=0.35 (FIG. 4).

Fourteen days following adoptive transfer, the number of CNS inflammatory foci in the fed CD4+ T cell and CD11b+ cell groups were significantly decreased compared to recipients of IgG control fed CD4+ T cells and CD11b+ groups (Table 1, CD4+ T cell AT control/CD11b+ cells vs utsekinumab).

Figure 5:
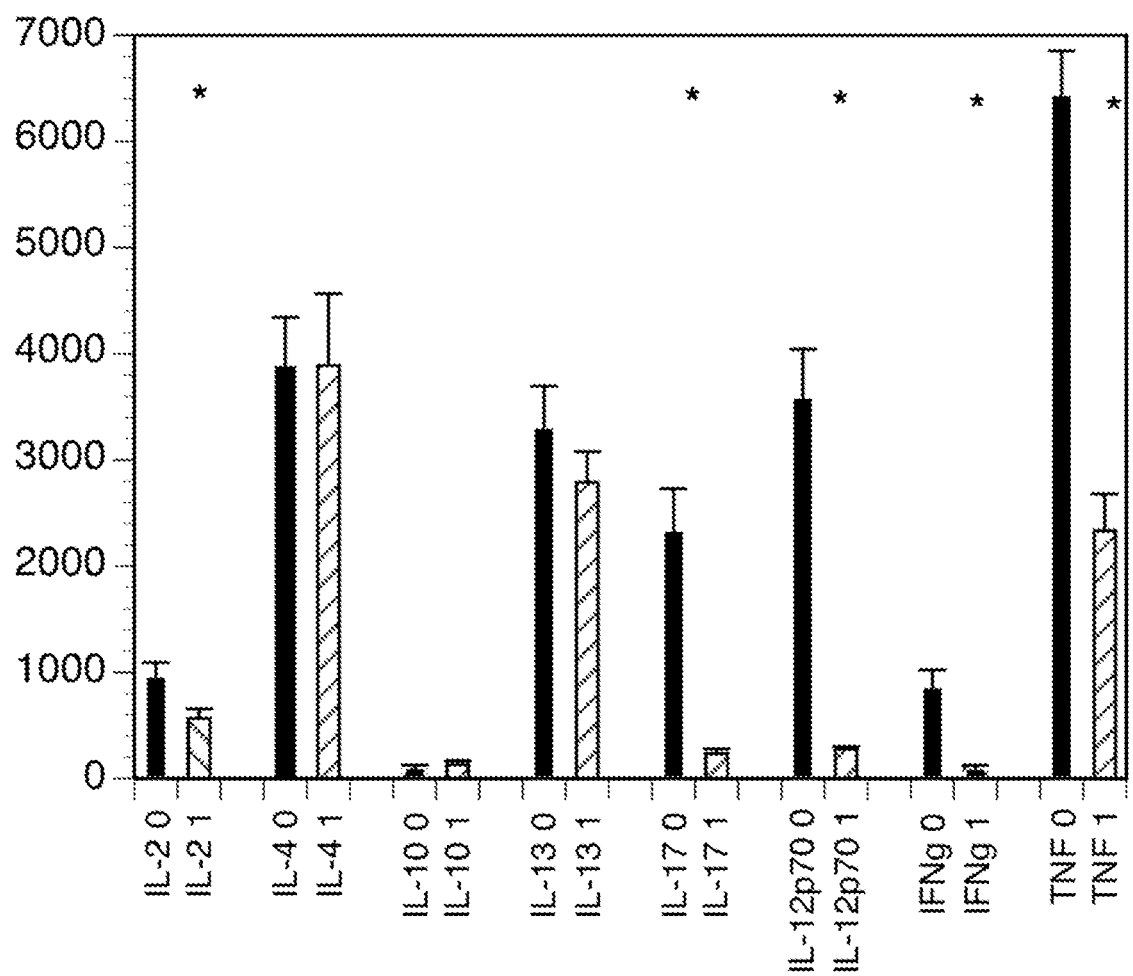
FIG. 5 shows that ingested ustekinumab decreases pro-inflammatory, Th1-like cytokines in the spleens of actively immunized mice. Lymphocytes isolated from spleen cells from IgG control fed mice or ustekinumab fed mice were stimulated with MOG peptide 35-55 and measured using an inflammatory cytokine antibody array as described in methods. Splenic lymphocytes showed decreased levels of Th1-like cytokines IL-2 ($p<0.03$), IFN-$\gamma$ ($p<0.01$), IL-12p70 ($p<0.005$), IL-17 ($p<0.005$), TNF-$\alpha$ ($p<0.005$). This experiment shows a combination of 3 separate experiments (total n=16/group). Results are expressed as pg/ml±SEM.
Figure 6:
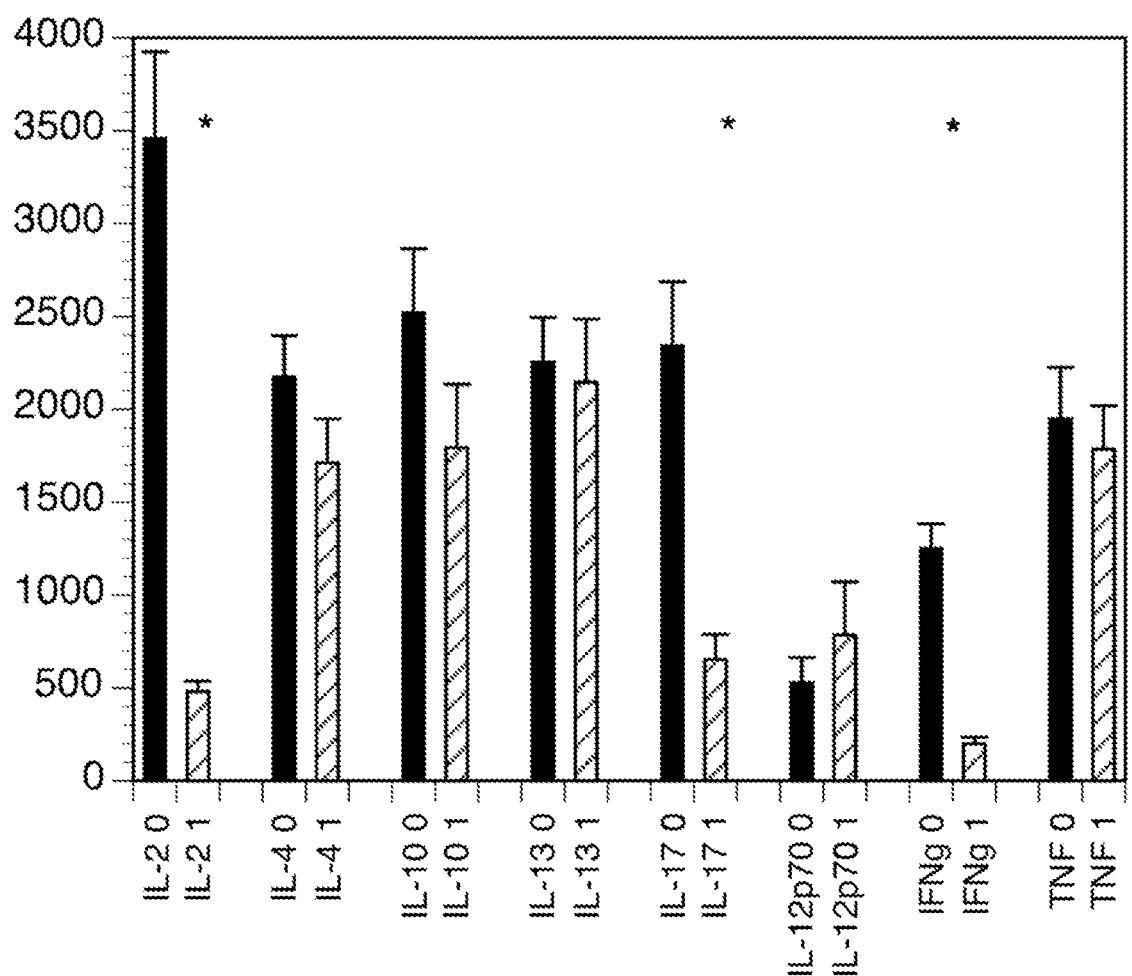
FIG. 6 shows that recipients of donor cells from ustekinumab fed mice show decreases in CNS Th1-like IFN-$\gamma$ cytokines, IL-12, IL-17 and increased Th2-like IL-10. Lymphocytes isolated from spinal cords from recipients of IgG control fed or ustekinumab fed donor cells were stimulated with MOG peptide 35-55 and measured using an inflammatory cytokine antibody array as described below. CNS lymphocytes showed decreased levels of Th1-like cytokines Th1-like cytokines IL-2 ($p<0.005$), IFN-$\gamma$ ($p<0.01$), IL-17 ($p<0.01$) in ustekinumab dosed vs IgG control dosed mice. This experiment shows a combination of 3 separate experiments (total n=16/group). Results are expressed as pg/ml±SEM.

Oral UTZ Decreases Pro-Inflammatory Cytokines in Ustekinumab Fed Mice and Increases Counter-Regulatory Cytokines in Recipients of Donor Cells from Ustekinumab Fed Mice The effect of oral ustekinumab on cytokines in actively fed and recipients of donor cells from ustekinumab fed mice was examined by comparing the cytokine profiles of MOG re-stimulated spleen and cord lymphocytes in IgG fed isotype control versus 1 mg ustekinumab fed mice. Splenic lymphocytes from actively fed mice showed significant decrease in levels of Th1-like cytokines IL-2, IL-12, IFN-g, IL-17 ($T_{eff}$) and in TNF-α in the ustekinumab fed group compared to the IgG control fed group (FIG. 5). CNS lymphocytes showed significant decreases in levels of Th1-like cytokine IL-2, IFN-γ, and IL-17 ($T_{eff}$) in the ustekinumab fed group compared to the IgG control fed group (FIG. 6). There were no significant changes in IL-4, IL-10, or IL-13 in active fed or recipients of donor cells from ustekinumab fed mice.

Figure 7:
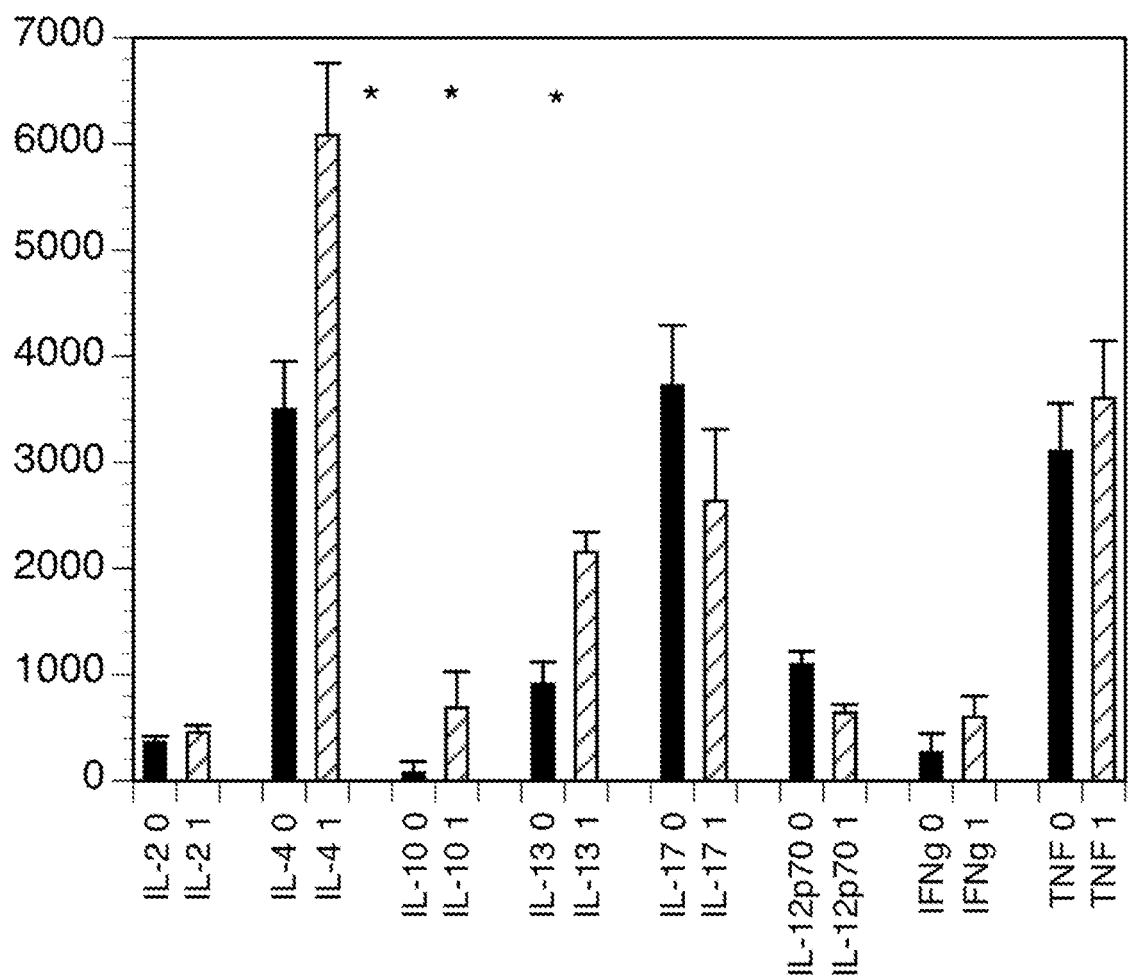
FIG. 7 shows that recipients of donor cells from ustekinumab fed mice show increases in counter regulatory cytokines IL-4, IL-10 and IL-13. Lymphocytes isolated from spleens from recipients of IgG control fed or ustekinumab fed donor cells were stimulated with MOG peptide 35-55 and measured using an inflammatory cytokine antibody array as described below. Splenic lymphocytes showed increased levels of Th2-like cytokines IL-4 ($p<0.01$), IL-10 ($p<0.01$), IL-13 ($p<0.01$) in ustekinumab dosed vs mock dosed mice. This experiment shows a combination of 3 separate experiments (total n=16/group). Results are expressed as pg/ml±SEM.
Figure 8:
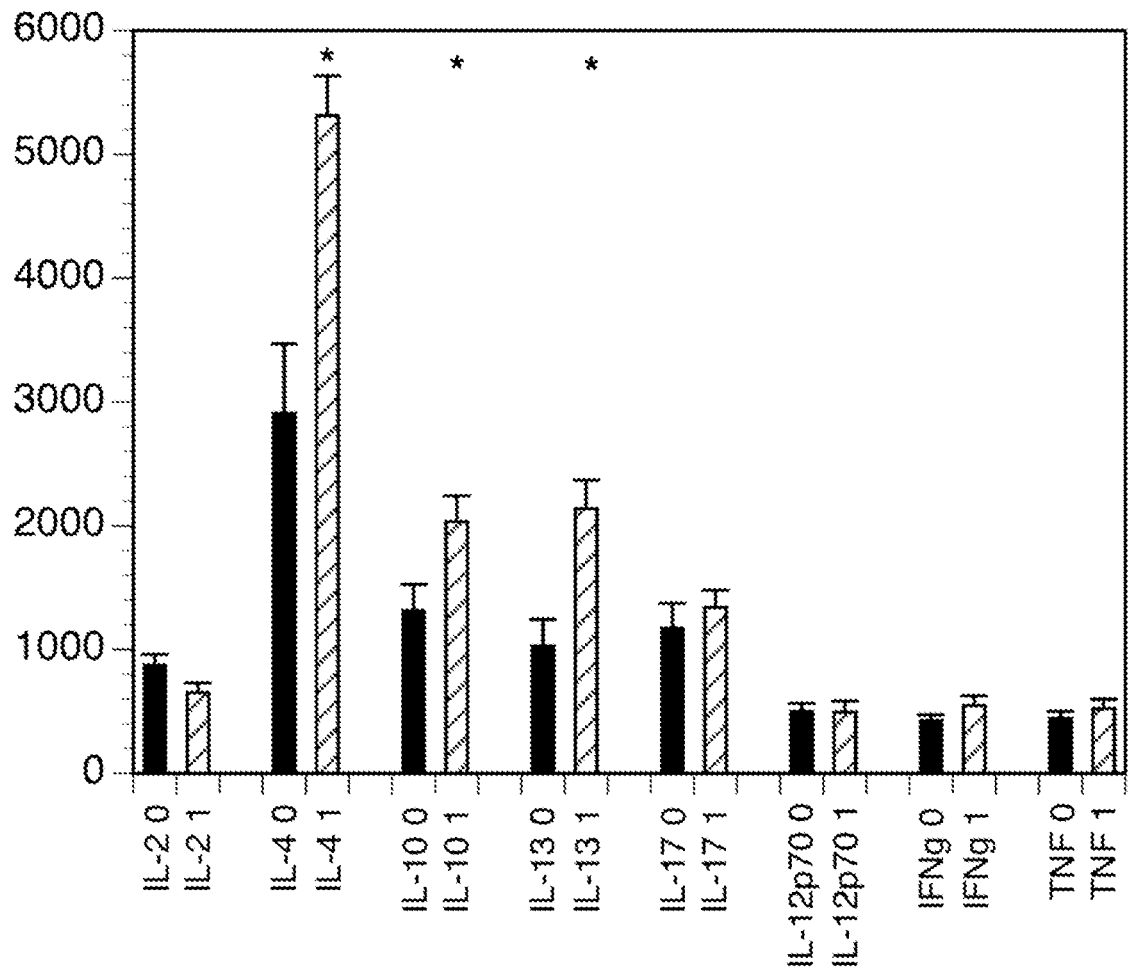
FIG. 8 shows that recipients of donor cells from ustekinumab fed mice show increases in CNS pro-inflammatory cytokines Th2-like IL-4, IL-10 and IL-13. Lymphocytes isolated from spinal cords from recipients of IgG control fed or ustekinumab fed donor cells were stimulated with MOG peptide 35-55 and measured using an inflammatory cytokine antibody array as described in methods. CNS lymphocytes showed increased levels of Th2-like cytokines IL-4 ($p<0.005$), IL-10 ($p<0.03$), IL-13 ($p<0.01$) in ustekinumab dosed vs mock dosed mice. This experiment shows a combination of 3 separate experiments (total n=16/group). Results are expressed as pg/ml±SEM.

The cytokine profiles of MOG re-stimulated spleen and cord lymphocytes in recipients of IgG control fed vs ustekinumab fed donor cells was examined. Splenic lymphocytes showed significant increases in levels of IL-4, IL-10 and IL-13 in ustekinumab fed groups compared to the IgG control fed group (FIG. 7). CNS lymphocytes showed significant increases in IL-4, IL-10 and IL-13 in the ustekinumab fed group compared to the IgG control fed group (FIG. 8). There were no significant changes in IL-2, IL-12, IFN-γ, IL-17 ($T_{eff}$) and TNF-α in active fed or recipients of donor cells from ustekinumab fed mice.

Recipients of Ustekinumab Fed Spleen CD4+ T Cells Produce More IL-4 and Recipients of Ustekinumab Fed Spleen CD11b+ Cells Produce Less IFN-g and TNF-α but More IL-4

Whether lymphocyte subsets showed differential activity on cytokine profiles was examined by investigating the cytokine profiles of MOG re-stimulated spleen lymphocytes in recipients of IgG control fed CD4+ T cells or CD11b+ vs ustekinumab fed CD4+ T cells or CD11b+ donor cells (FIGS. 3-4). Recipient splenic lymphocytes showed significant increases in levels of IL-4 after both CD4+ T cells and CD11 b+ transfer in ustekinumab fed groups compared to the IgG fed group. Splenic lymphocytes also showed significant decreases in IFN-g and TNF-α in the CD11b+ ustekinumab fed group compared to the CD11b+ IgG fed group (Table 2). There were no significant changes in IL-2, IL-10, IL-12, IL-13, IL-17 in recipient spleen after CD4+ T cell or CD11 b+ from ustekinumab fed donors (data not shown).

TABLE 2

Spleen cells in recipients of CD4+ or CD11b+ lymphocytes from ustekinumab fed donors show increased IL-4 and decreased IFN-γ and TNF-α

|  | Recipients of IgG control fed donor cells | Recipients of ustekinumab fed donor cells |
|---|---|---|
| CD4+ T cell |  |  |
| TNF-a | 304 ± 44 | 306 ± 68 |
| IL-4 | 202 ± 43 | 2476 ± 378* |
| IFN-g | 392 ± 96 | 511 ± 90 |

TABLE 2-continued

Spleen cells in recipients of CD4+ or CD11b+ lymphocytes
from ustekinumab fed donors show increased IL-4
and decreased IFN-γ and TNF-α

|  | Recipients of IgG control fed donor cells | Recipients of ustekinumab fed donor cells |
|---|---|---|
| Macrophage (CD11b+) | | |
| TNF-a | 810 ± 96 | 527 ± 12* |
| IL-4 | 441 ± 96 | 1227 ± 14* |
| IFN-g | 474 ± 128 | 206 ± 48* |

*$p < 0.001$; n = 12/group.
Results are expressed as pg/ml ± SEM.

There were no significant changes in IL-2, IL-10, IL-12, IL-13, IL-17 or TNF-α.

Actively Ustekinumab Fed or Recipients of Ustekinumab Fed Cells Show No Significant Increase in CD4$^+$CD25$^+$FoxP3$^+$ Cell Frequency or TGF-β Secretion Whether immunomodulation was due to an increased T$_{reg}$ frequency or increased TGF-β secretion was determined by examing if CD4$^+$CD25$^+$FoxP3$^+$ T$_{reg}$ might be induced by ustekinumab feeding and explain protection in actively treated and recipients of adoptively transferred cells from ustekinumab fed donors. FACS analysis shows no significant increase in splenic CD4$^+$CD25$^+$FoxP3$^+$ cell frequency in ustekinumab fed compared to IgG control fed mice in actively fed or recipients of actively fed donor cells.

Whether there was increased secretion of TGF-β in MOG re-stimulated spleen and cord lymphocytes from actively treated and recipients of adoptively transferred cells from ustekinumab fed donors examined. There was no effect on TGF-β secretion after active ustekinumab feeding in spleen or in spinal lymphocytes compared to control (data not shown). There was also no effect on TGF-β secretion in spleen or in spinal lymphocytes from recipients of ustekinumab feed donors compared to control.

DISCUSSION

The present invention shows an overall anti-inflammatory effect of ingested ustekinumab in MOG immunized mice. Both 1 mg and 10 mg ingested (oral) ustekinumab showed a significant effect with 1 mg demonstrating the most robust activity. Adoptive transfer of ustekinumab fed MOG-re-stimulated splenocytes, CD4$^+$ T cells or CD11b$^+$ into recipient mice with early clinical disease suppressed ongoing disease. Both active treatment with oral ustekinumab or adoptive transfer of splenocytes, CD4$^+$ T cells and CD11b$^+$ from ustekinumab fed donors showed significantly less CNS inflammation in the ustekinumab groups compared to IgG control fed mice.

There was a decrease in pro-inflammatory Th1-like and TNF-α cytokines in actively fed immunized mice and increases in Th2-like counter-regulatory cytokines IL-4, IL-10, or IL-13 in recipients of donor cells from fed mice. Recipients of both CD4+ T cells and CD11 b$^+$ cells from ustekinumab fed donors produce increased IL-4 activity without increased T$_{reg}$ or TGF-β.

Th1 T cells secrete IL-2 and IFN-g upon stimulation, uses IL-2 as a growth factor and regulate DTH response and inflammation in EAE (28). High levels of IFN-g-specific message are expressed in T cells isolated from the CNS of the recipient MOG-activated RAG-1−/− mice with EAE (29) Inoculation of B6 mice with MOG peptides can activate pathogenic neuroantigen-specific Th1 T helper cells in vivo and produces inflammation in murine EAE (27).

EAE also demonstrates high mRNA expression IL-12 in PMNC and CNS [30]. IL-12 stimulates myelin-reactive encephalitogenic T cells with CNS-infiltrating properties (31), drives antigen specific cells (32) important in CNS inflammation (30) and contributes to macrophage mediated disease exacerbation (33). APC produced IL-12p70 induces Th1-like cells [34]. Antibody inhibition of endogenous IL-12 in vivo prevents paralysis (35). Blockade of the p40 subunit used by IL-12 might be expected to block the generation of Th1-like pro-inflammatory cytokines.

IL-23 expression is critical in EAE (36, 37). IL-23 enhances IL-17 expression [Liu, 2005 #4649] in activated DC and phagocytic cells (38). In humans, IL-23 induces memory lymphocytes to expand into Th17 phenotype with a subpopulation of Th1/Th17. Lymphocytes from relapsing MS subjects can expand into Th1 (T-bet)/Th17 (RORg) cells and are in MS brain tissue (39). Blocking IL-23 activity inhibits expansion of IL-17 producing cells (40). Blockade of the p40 subunit used by IL-23 might be expected to block the generation of Th17 pro-inflammatory cells.

TNF-α is important in CNS pathology in EAE (41-43) as part of a functional 'type 1 cytokine' unit (44). Adoptive transfer of EAE with TNF-α producing cells contributes to CNS inflammation (45, 46). The reduction of TNF-α activity decreases the severity of EAE (47). In humans, inhibition of DC IL-23 is associated with decreased TNF-α production (36). Blockade of the p40 subunit used by IL-23 might be expected to block the generation of TNF-α producing cells.

Th2-like lymphocytes produce IL-4 (48), IL-10 and IL-13 (48) and inhibit EAE (49). DC derived from Peyer's patch (PP) in particular CD11b+(50, 51) but not from spleen, produce IL-4 (52) and IL-10 (Th2-like) and low levels of IFN-γ (53) compared with spleen DCs (53). Regulatory PP (CD45RB$^{low}$CD4$^+$ T[h2-like] cells) can produce IL-10 and can suppress proliferation of purified peripheral LN T cells (54). Splenic IL-13 reduces infiltrating mononuclear cells into CNS during EAE (55), inhibits PBMC production of IL-12 (56) and down-regulates monocyte/macrophage activities at sites of inflammation (57)

The blockade of IFN-γ can increase IL-4 production (58, 59) showing that these two cytokines exert opposite regulatory effects (60). IFN-γ also inhibits IL-10 production by monocytes (61). This data suggests that blockade of Th1-like cytokines may also allow IL-13 production. Overall, the blockade of Th17 production by inhibiting IL-23 activity and of Th1 IFN-γ by inhibiting IL-12 activity in the GALT by UTZ could disinhibit Th2-like cytokine production in GALT and systemically.

Previous investigators have not shown anti-inflammatory activity using psoriasis effective parenteral doses of ustekinumab in MS (17). The lack of response was attributed in part to the inability of the antibody to reach the CNS (62). In contrast, the present invention demonstates the unexpected effect that oral ustekinumab, presumably delivered to DC in subepithelial dome region (63-65) or CD4+ T cells in interfollicular T cell regions of PP (66-68) can up-regulate Th2-like cytokines, in particular IL-4 cell populations in the spleen.

Hormetic responses were observed with oral IFN-α (61), oral somatostatin in EAE (9), oral SIRS peptide 1-21 in the NOD mouse (6) and oral ustekinumab. Immune-system-related hormetic-like biphasic dose-response relationships (U shaped dose response curve with decreasing clinical activity with increasing doses) are common, reported in over 30 animal models, and little appreciated compared to dose response models (70, 71). Hormesis may be a common response when immune-active proteins are administered by the oral route in autoimmune diseases or their mouse models.

The following references are cited herein.
1. Alvord et al., Ann NY Acad Sci. 1965; 122:333-45.
2. Raine et al., NY State J Med. 1977; 77:1693-6.
3. Wisnewski et al., Ann Neurol. 1977; 1:144-8.
4. Feuer et al., J Neuroimmunol. 1985; 10:159-66.
5. Brod et al., Neurology. 1994; 44:1144-8.
6. Brod et al., J Interferon Cytokine Res. 2008; 28:25-30.
7. Brod et al., J Neuroimmunol. 2008; 1 93:106-12.
8. Brod et al., J Neuroimmunol. 2011; 232:131-5.
9. Brod et al., Autoimmunity. 2011; 44:437-43.
10. Brod et al., J Neuroimmunol. 1995; 58:61-9.
11. Brod et al., Cytokine. 2014; 68:86-93.
12. O'Neill et al., Biologics: Targets & Therapy. 2009; 3:159-68
13. Zaghi et al., Journal of Drugs in Dermatology: JDD. 2012; 11:160-7.
14. Chien et al., Drugs. 2009; 69:1141-52.
15. Yeilding et al., Ann N Y Acad Sci. 2011; 1222:30-9.
16. Ryan et al., Expert Opinion on Biological Therapy. 2010; 10:587-604.
17. Segal et al., Lancet Neurol. 2008; 7:796-804.
18. Leonardi C et al., Lancet. 2008; 371:1665-74.
19. Kavanaugh et al., Curr Med Res Opin. 2010; 26:2385-92.
20. Uhlenhake et al., Expert Opinion on Biological Therapy. 2010; 10:1105-12.
21. Young et al., Expert Review of Clinical Immunology. 2011; 7:9-13.
22. Gordon et al., J Am Acad Dermatol. 2012; 66:742-51.
23. Lebwohl et al., J Am Acad Dermatol. 2012; 66:731-41.
24. Papp et al., The British Journal of Dermatology. 2013; 168:844-54.
25. Yeilding et al., Ann N Y Acad Sci. 2012; 1263:1-12.
26. Ritchlin et al., Ann Rheum Dis. 2014; 73:990-9.
27. Tompkins et al., Journal of Immunology. 2002; 168: 4173-83.
28. Cher et al., Journal of Immunology. 1987; 138:3688-94.
29. Yura et al., The British Journal of Dermatology. 2001; 145:966-73.
30. Issazadeh et al., J Neuroimmunol. 1996; 69:103-15.
31. Bagaeva et al., J Neuroimmunol. 2003; 137:109-16.
32. Segal et al., The Journal of Experimental Medicine. 1996; 184:771-5.
33. Smith et al., Am J Path. 1997; 150:1909-17.
34. Pellegrini et al., Transpl Immunol. 2003; 12:49-61.
35. Leonard et al., The Journal of Experimental Medicine. 1995; 181:381-6.
36. Vaknin-Dembinsky et al., Journal of Immunology. 2006; 176:7768-74.
37. Langrish et al., The Journal of Experimental Medicine. 2005; 201:233-40.
38. Hunter et al., Nat Rev Immunol. 2005; 5:521-31.
39. Kebir et al., Ann Neurol. 2009; 66:390-402.
40. Kuchar et al., Proteins. 2014; 82:975-89.
41. Renno et al., Journal of Immunology. 1995; 154:944-53.
42. Issazadeh et al., J Neurosci Res. 1995; 40:579-90.
43. Okuda et al., J Interferon Cytokine Res. 1998; 18:415-21.
44. Qiu et al., Am J Pathol. 2001; 158: 1503-15.
45. Waldburger et al., Am J Pathol. 1996; 148:375-82.
46. Held et al., J Autoimmun. 1993; 6:311-22.
47. Selmaj et al., Ann Neurol. 1991; 30:694-700.
48. Malefyt et al., The Journal of Experimental Medicine. 1991; 174:915-24.
49. Monney et al., Nature. 2002; 415:536-41.
50. Kelsall et al., Immunol Rev. 2005; 206:132-48
51. Iwasaki et al., Journal of Immunology. 2001; 166:4884-90.
52. Everson et al., J Interferon Cytokine Res. 1998; 18:103-15.
53. Iwasaki et al., The Journal of experimental medicine. 1999; 190:229-39.
54. Jump et al., Journal of immunology. 2002; 168:6113-9.
55. Offner et al., Journal of Immunology. 2005; 175:4103-11.
56. D'Andrea et al., The Journal of Experimental Medicine. 1995; 181:537-46.
57. Hart et al., Clin Exp Immunol. 1995; 99:331-7.
58. Mu et al., Immunology. 1994; 83:639-45.
59. Larner et al., Journal of Immunology. 1993; 150:1944-50.
60. Parronchi et al., Journal of Immunology. 1992; 149: 2977-83.
61. Chomarat et al., The Journal of Experimental Medicine. 1993; 177:523-7.
62. Martin et al., Lancet Neurol. 2008; 7:765-6.
63. Kelsall et al., The Journal of Experimental Medicine. 1996; 183:237-47.
64. Nagatani et al., Immunobiology. 2011; 216:416-22.
65. Nagatani et al., Ann N Y Acad Sci. 2004; 1029:366-70.
66. Shreedhar et al., Infect Immun. 2003; 71:504-9.
67. Soni et al., Journal of Controlled Release 2006; 115:68-77.
68. Awaad et al., International Journal of Nanomedicine. 2012; 7:1423-39.
69. Brod et al., J Interferon Cytokine Res. 1999; 19:841-52.
70. Calabrese et al., Grit Rev Toxicol. 2005; 35:89-295.
71. Calabrese et al., Environ Pollut. 2005; 138:379-411.
72. Freireich et al., Cancer Chemother. Rep. 1966; 50:219-244.
73. Watanabe et al., Risk Analysis 1992; 12:301-310.
74. Mahmood et al., J Clinical Pharm 2003; 43(7):692-697.

While the invention has been described with reference to certain embodiments, those skilled in the art will appreciate that modifications may be made without departing from the scope of the invention. All patents and publications cited in this specification are indicative of the level of those skilled in the art to which the invention pertains.

What is claimed is:

1. A method for treating rheumatoid arthritis in a human subject comprising orally administering to the subject a therapeutically effective amount of ustekinumab.

2. The method of claim 1, wherein ustekinumab is administered in a dose from about 0.001 mg to about 50 mg.

3. The method of claim 2, wherein ustekinumab is administered in a solid or liquid form.

4. The method of claim 1, wherein said ustekinumab administration decreases levels of interleukin-2, interleukin-12, tumor necrosis factor-α, and interferon-γ.

5. The method of claim 1, wherein said ustekinumab administration increases levels of interleukin-4, interleukin-10 and interleukin-13.

6. A method for decreasing levels of innate inflammatory cytokines that are interleukin-1β and tumor necrosis factor-α, Th1-like cytokines that are interleukin-2, interleukin-12, interferon-γ, interleukin-17 $T_{eff}$, and interleukin-12p70 and increasing levels of Th2-like counter-regulatory cytokines that are interleukin-4, interleukin-10, and interleukin-13 in a human subject, comprising the step of:

orally administering to the subject a therapeutically effective amount of ustekinumab.

7. The method of claim 6, wherein the subject has rheumatoid arthritis, type 1 diabetes, systemic lupus erythematosus, transplant rejection, autoimmune thyroid disease, sarcoidosis, scleroderma, granulomatous vasculitis, Crohn's disease, ulcerative colitis, Sjogren's disease, ankylosing spondylitis, polymyositis dermatomyositis, polyarteritis nodosa, immunologically mediated blistering skin diseases, Behcet's syndrome, multiple sclerosis, systemic sclerosis, Goodpasture's disease or immune mediated glomerulonephritis.

8. The method of claim 6, wherein said ustekinumab is administered in a dose from about 0.001 mg to about 50 mg.

9. The method of claim 6, wherein ustekinumab is administered in a solid or liquid form.

* * * * *